(12) United States Patent
Bowen

(10) Patent No.: US 6,361,553 B1
(45) Date of Patent: Mar. 26, 2002

(54) ICE PACK WITH EXPANDABLE OPENING

(75) Inventor: Michael L. Bowen, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/471,532

(22) Filed: Dec. 23, 1999

(51) Int. Cl.⁷ ................................................. A61F 7/00
(52) U.S. Cl. ........................ 607/112; 607/114; 607/108
(58) Field of Search ............................... 607/108, 112, 607/114; 383/120, 85, 33

(56) References Cited

U.S. PATENT DOCUMENTS

| 446,518 A | * | 2/1891 | Hesser |  |
| 768,340 A | * | 8/1904 | Ormsbee, Jr. |  |
| 1,897,025 A | * | 2/1933 | Palmer |  |
| 4,911,560 A |  | 3/1990 | Hoover et al. |  |
| 4,946,290 A | * | 8/1990 | Matyja | 383/10 |
| 5,356,426 A | * | 10/1994 | Delk et al. | 607/112 |

FOREIGN PATENT DOCUMENTS

CH   130910   1/1929

OTHER PUBLICATIONS

PCT Search Report dated Mar. 29, 2001.

* cited by examiner

Primary Examiner—Linda C. M. Dvorak
Assistant Examiner—Jocelyn Ram
(74) Attorney, Agent, or Firm—Dority & Manning, P.A.

(57) ABSTRACT

An ice pack generally intended for single patient use includes an elongated bag member defined by opposite side panels. The bag member has a closed end and an open opposite end. The open end is used for introducing ice into the bag member by pulling the side panels apart at the open end. A portion of at least one of the side panels generally adjacent to the open end is expandable from a first width defined between sealed edges of the bag member to an increased width so as to provide a greater effective cross-sectional area to the opening in order to aid in filling the ice pack.

18 Claims, 4 Drawing Sheets

ICE PACK WITH EXPANDABLE OPENING

BACKGROUND OF THE INVENTION

The present invention relates generally to relatively small ice packs intended for single patient use.

Single patient ice packs are generally known in the art. One such ice pack is manufactured and sold by Tecnol Medical Products, Inc. and is described in U.S. Pat. No. 4,347,848. These ice packs are particularly designed for application of "cold" locally at particular points on the body.

Because of their size, these smaller ice packs typically have small openings. The openings are also limited in size due to the difficulty of making a water tight seal across a larger opening. The small openings are, however, troublesome in certain other respects. For example, these ice packs are typically filled from an automatic ice machine or from a scoop from an ice bin. The relatively small opening tends to make the filling operation difficult. A larger opening would be beneficial and render the ice packs more "user friendly." However, it is more difficult to provide a water tight seal to such a larger opening.

With the conventional ice packs, such as the ice pack described in the '848 patent cited above, a closure clip is provided for sealing the opening of the ice pack. A larger clip could be provided to seal a larger opening, however, at some length, the larger clips become cost prohibitive and physically uncomfortable to patients.

Accordingly, the industry would benefit from a small, single patient ice pack having the benefits of a large opening without the sealing problems associated with such a large opening.

SUMMARY OF THE INVENTION

Objects and advantages of the invention will be set forth in part in the following description, or may be obvious from the description, or may be learned through practice of the invention.

In accordance with the invention, an ice pack, such as a relatively small single patient use ice pack, is provided. In one embodiment, the ice pack includes an elongated bag member defined by opposite side panels. The panels are sealed generally along the longitudinal edges thereof and at a first end thereof. The panels are open at the opposite end to define the opening for the bag. This opening is used to introduce ice into the bag member. The opening is "defined" or established by an operator pulling the side panels apart in proximity of the open end. In order to provide a larger effective cross-sectional area for the opening upon pulling the side panels apart, a portion of at least one of the side panels generally adjacent to the open end is expandable from a first width defined between the sealed edges to an increased width without actually increasing the distance between the longitudinally edges.

In a particularly useful embodiment, the expandable portion of the side panel includes a longitudinally extending expandable structure defined in the side panel such that the side panel expands essentially only along the expandable structure. For example, the expandable structure may include a longitudinally extending gathering of material that forms the side panel. This "gathering" may, for example, include a longitudinally extending fold or pleat line. This fold line may include multiple folds of the material.

For ease of manufacture of an ice pack according to the invention, the longitudinally extending expandable structure may have an effective length less than the full longitudinal length of the side panel. For example, in one embodiment, the longitudinally extending structure may comprise a longitudinally extending gathering of material, such as a fold line, that extends generally along the full longitudinal length of the panel but is sealed from the first sealed end to a position near the opening in the bag member. The unsealed length thus defines the effective length of the longitudinally extending expandable structure.

In another embodiment according to the invention, each of the side panels may include the expandable portion. For example, each of the side panels may include the expandable gathering of material or fold line.

It should be appreciated that an ice pack made according to the present invention may include any desired feature from conventional ice packs. For example, the ice pack may also include tie members that extend longitudinally from each of the ends of the bag member, as described in the '848 patent.

It should also be appreciated that the present invention is not limited to any particular type of material or method of manufacture. For example, the expandable portion or structure can be defined in any conventional bag material, including the materials described in the '848 patent.

The invention will be described in greater detail below through use of the appended figures.

DETAILED DESCRIPTION

Figure 1:
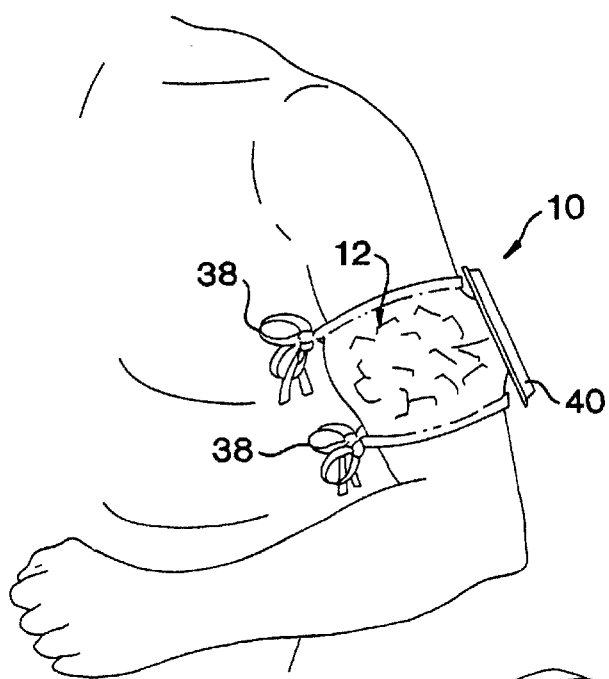
FIG. 1 is a perspective view of an improved ice pack particularly showing the ice pack in use and applied on the arm of a patient.

Reference will now be made in detail to the presently preferred embodiments of the invention, one or more examples of which are illustrated in the drawings. Each example is provided by way of explanation of the invention, and not meant as a limitation of the invention. For example, features illustrated or described as part of one embodiment can be used on another embodiment to yield a still further embodiment. It is intended that the present application include such modifications and variations.

An improved ice pack according to the invention is illustrated as ice pack 10 in the figures. FIG. 1 shows ice pack 10 in actual operation. In this particular application, ice pack 10 is fastened to the arm of the patient by means of a pair of tie strings 38 that extend longitudinally from each end of ice pack 10, as shown in greater detail in FIG. 2. A closure member, such as a clip 40, is also shown in its closed operational position whereby it seals an open end of ice pack 10.

Referring to FIGS. 2 through 5, ice pack 10 according to the invention is of the type commonly employed for single patient use in the application of cold therapy to relatively small areas of the body. Ice pack 10 defines a generally rectangular envelope or bag member 12 having first and second sides 14, 16. Sides 14, 16 are sealed along edges 19 and define a closed or sealed end 18 and an opposite open end 20. As mentioned, tie strings 38 may extend longitudinally outward from each of the ends 18, 20 so that ice pack 10 may be readily applied to a particular area of the patient, as illustrated in FIG. 1.

Ice pack 10 according to the present invention may be constructed of any suitable materials and by any applicable process. For example, ice pack 10 according to the invention may be formed of the materials and by the process described in U.S. Pat. No. 4,347,848. (The '848 patent is incorporated herein by reference in its entirety for all purposes.) For example, as described in the '848 patent, ice pack 10 according to the invention may include a waterproof bag made of polyethylene or other relatively inexpensive waterproof material formed internally of sides 14, 16. The polyethylene material may be bonded to an intermediate layer of absorbent material which, in turn, may be bonded to an outer layer of absorbent material perforated with a multitude of small holes. These holes give the material a wicking effect and permit evaporation of water condensing in the intermediate layer at the polyethylene interface so that the outside of the ice pack does not become wet and unsuitable for reuse because of condensation. This type of construction is described in greater detail in the '848 patent.

The present ice pack 10 is also not particularly limited in its overall configuration or shape. For example, the rectangular bag member 12 is merely an example of a suitable configuration. Bag 12 may include a throat section 32 that diverges from a central portion of bag member 12 to the open end 20. This throat section 32 may be desirable for filling ice pack 10 with a funnel, scoop, or the like.

One method of sealing the open ends of conventional ice packs is through the use of a clip or closure member generally illustrated as 40 in the figures. Any conventional clip or closure member may be utilized in this regard. A suitable clip is described in detail in the '848 patent. Briefly, in operation the clip is positioned against one side of ice pack 10 and is held in position by any suitable device, such as a piece of tape or adhesive, to hold a blade-like member 41 in proper position. The extending throat section 32 is then folded over blade-like member 41 and a sheath member 43 is then closed onto blade-like member 41 to seal the bag member between the two components. Sheath member 43 has a width slightly less than blade-like member 41 and, thus, the portion of throat section 32 held between the components is compressed and sealed. Sheath member 43 is latched onto blade-like member 41 by any suitable latching mechanism 45. Ice pack 10 is unsealed simply by releasing latch mechanism 45 for subsequent refilling and reuse.

An important aspect of the present invention is that it provides a larger opening into the bag member without increasing the overall size of the ice pack. Structure is provided in at least one of side panels 14, 16 generally adjacent to open end 20 for defining a greater cross-sectional area for an opening 22 into bag member 12, as particularly illustrated in FIG. 4. This structure includes an expandable portion configured in at least one of the side members. This expandable portion expands from a first width defined between sealed edges 19 to an increased second width while maintaining essentially the same distance between sealed edges 19, thereby defining the greater cross-sectional area for opening 22. The expandable portion is illustrated generally as component 24 in the figures and may take on various structural configurations. For example, the expandable portion 24 may comprise a longitudinally extending expandable structure 26 defined in one of the side panels such that the respective panel expands essentially along the longitudinal structure. The longitudinal structure may be defined by a longitudinally extending gathering of the material forming the respective side panel. This gathering may, for example, be defined by pleats, folds, and the like. In the embodiment illustrated in the figures, the longitudinally expanding structure 26 is defined by at least one fold in at least one of the side panels. The fold defines a fold line 28. Multiple folds may be defined instead of one relatively large fold.

As illustrated in the figures, each of the side panels 14, 16 may include the expandable structure. For example, each of the sides 14, 16 may include its own respective folds. Depending on the size of opening 22 desired, it may only be necessary to include the expandable structure in one of the sides 14, 16.

The folds or gathering of the side panel material defining the expandable structure may be defined initially by folding or gathering the side panels along the interior longitudinal length thereof. Subsequently, a portion of the longitudinal folds or gathering may be sealed along a sealed portion 36 up to a point 37. It may be desired to seal the folds along portion 36 so as to prevent a "ballooning" of bag member 12 when filled with ice. In this regard, the longitudinal expanding structure thus has an effective length defined essentially from point 37 to the open end 20. Point 37 may be defined anywhere along the longitudinal length of the fold lines, but should be positioned so that the expandable structure takes effect in throat section 32, as particularly illustrated in FIG. 4. Sealed portion 36 may be sealed by any conventional manner, including a heat seal, adhesives, and the like.

Figure 2:
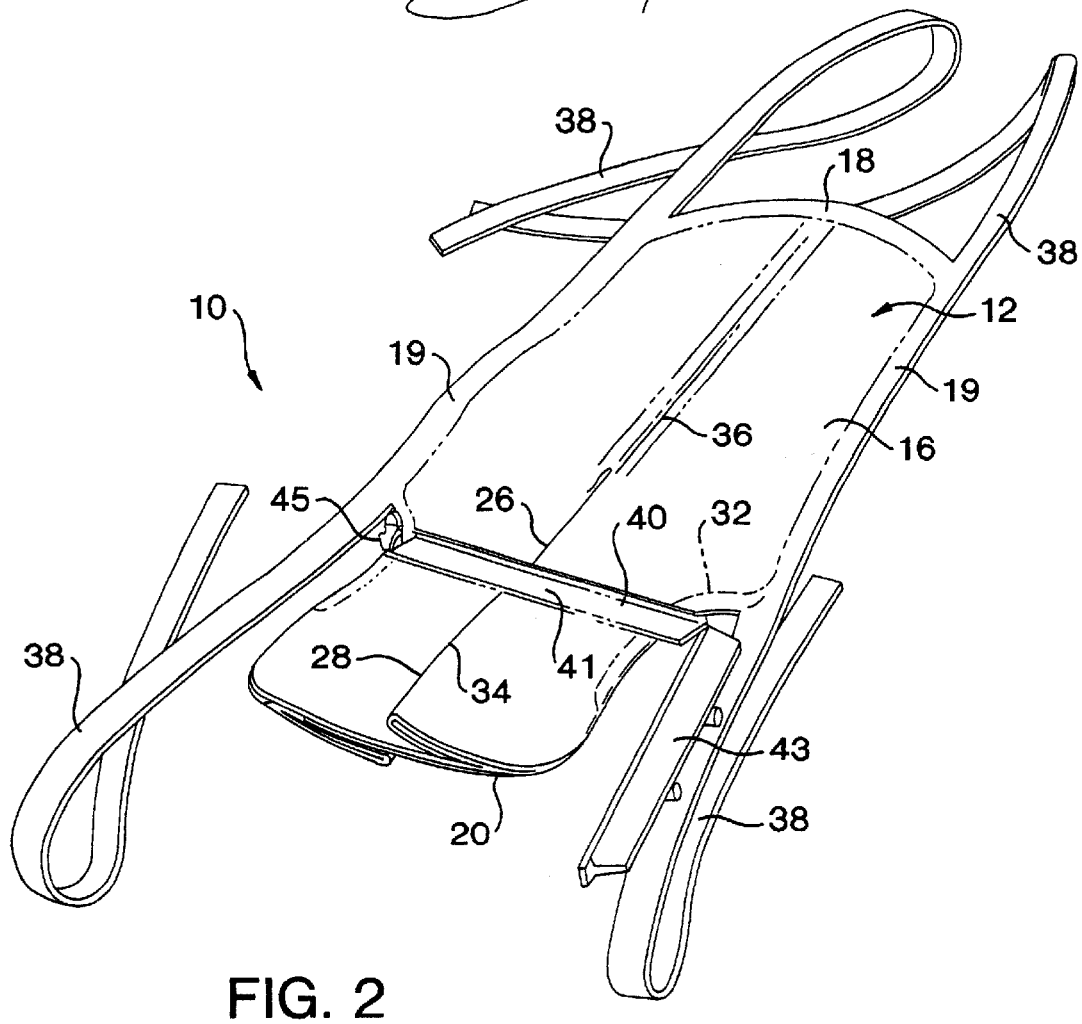
FIG. 2 is a perspective view of the ice pack particularly illustrating folded longitudinal portions of the side panels as seen from the opening in the bag member.
Figure 3:
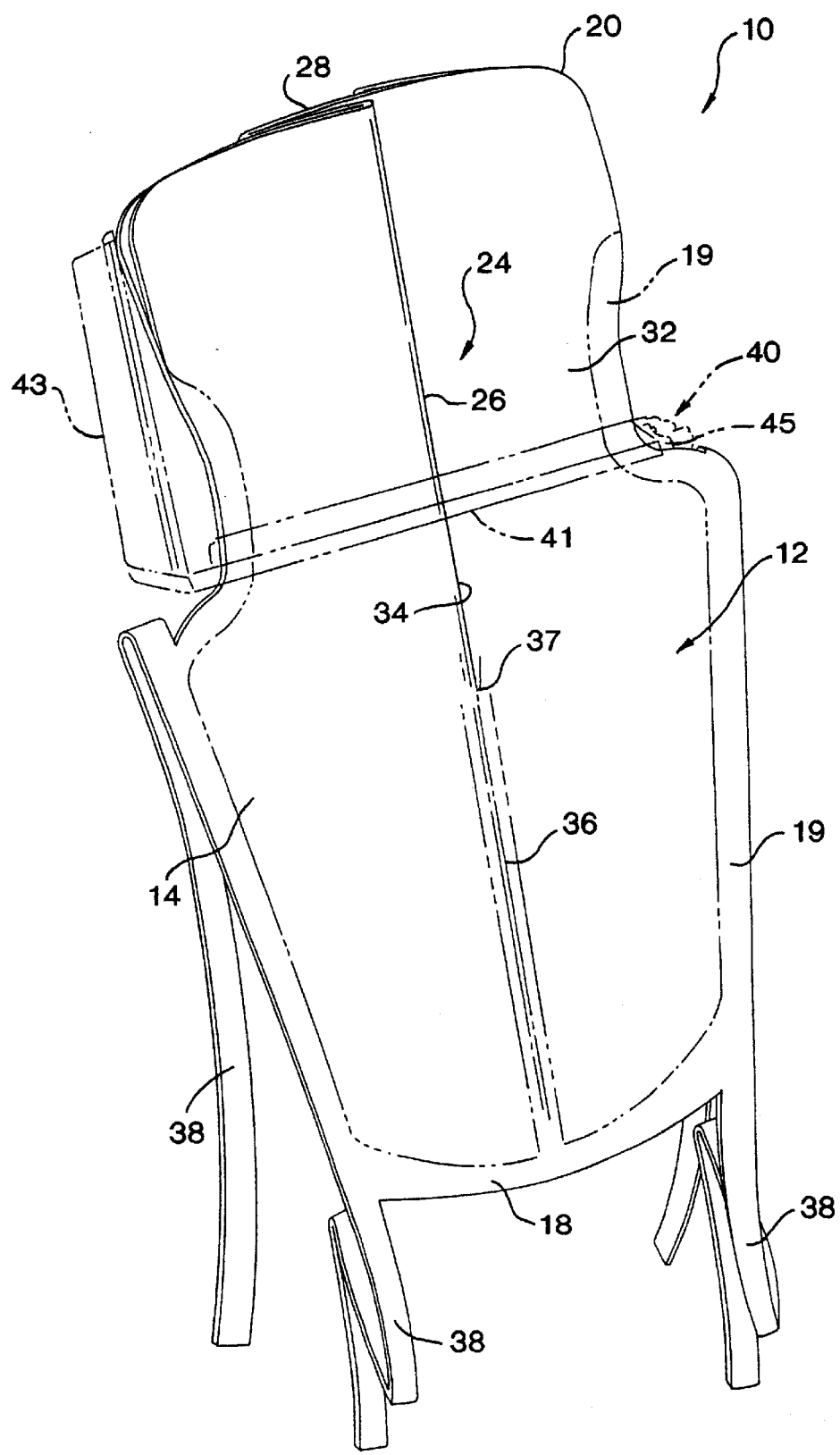
FIG. 3 is an additional perspective view of the ice pack particularly illustrating the effective length of the longitudinally extending expandable structure.
Figure 4:
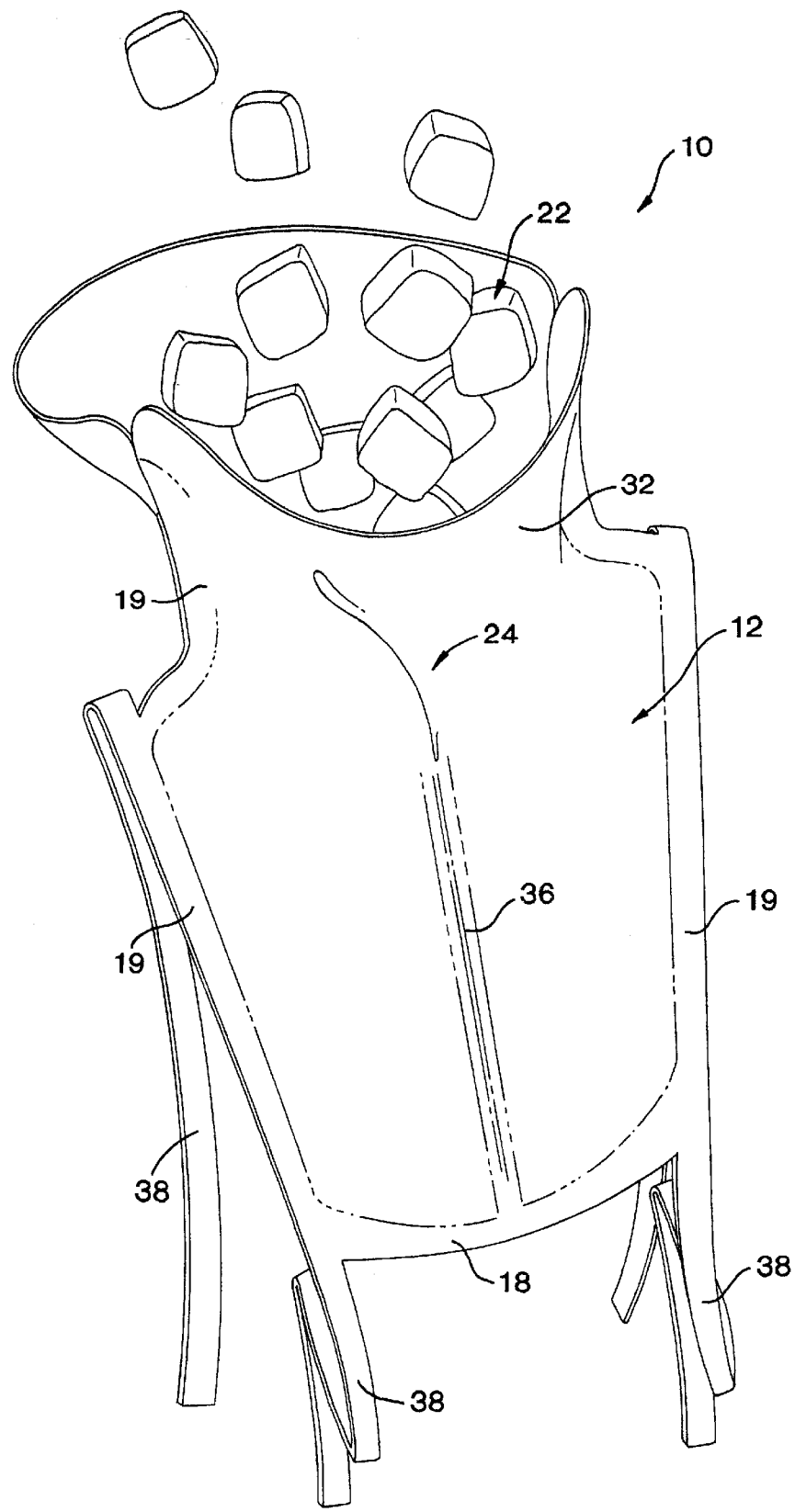
FIG. 4 is a perspective view of the ice pack particularly illustrating the opening in its expanded enlarged state while being filled with ice.
Figure 5:
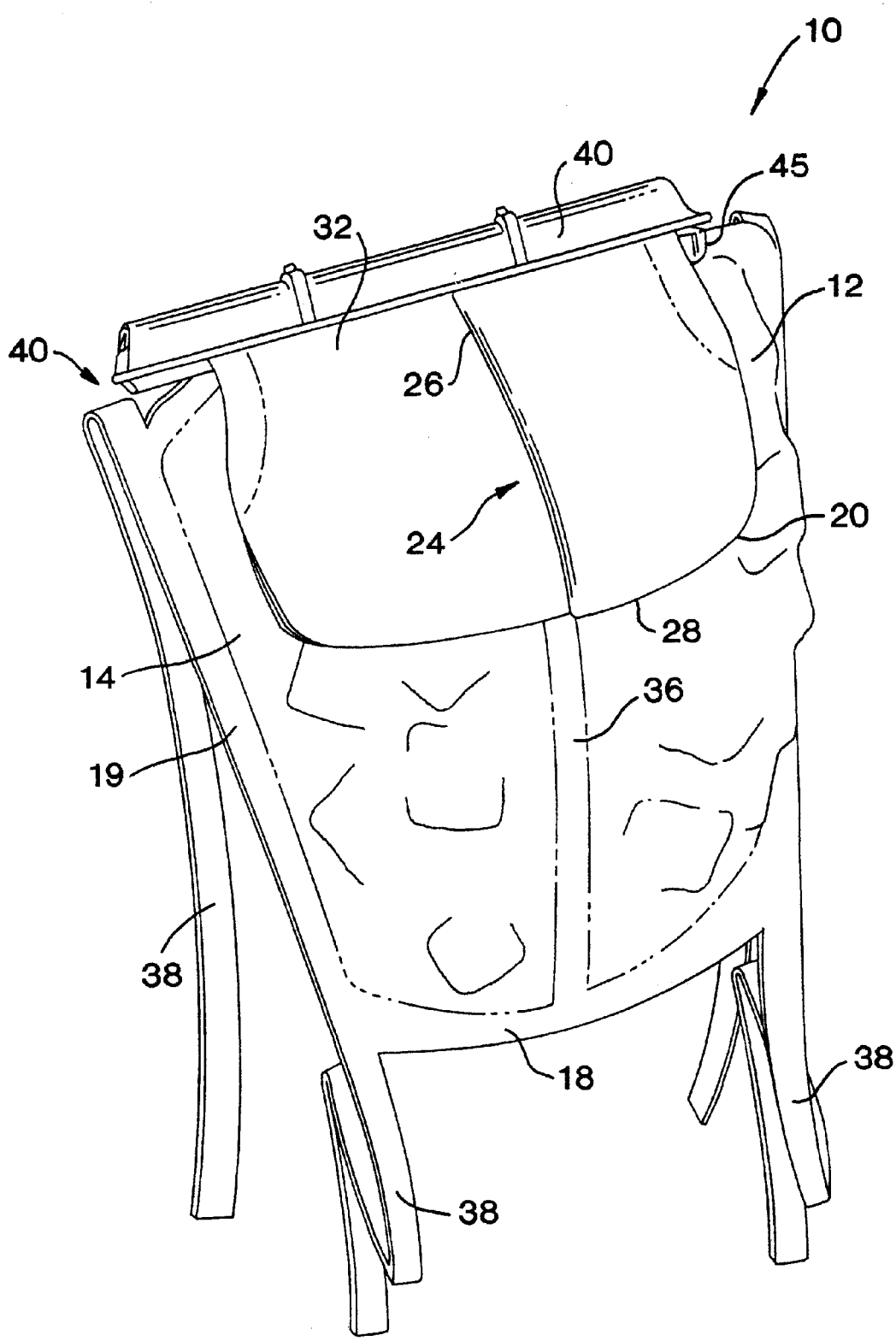
FIG. 5 is a perspective view of the filled and sealed ice pack according to the invention.

Defining the expandable portion 24 of the side panels as longitudinally extending folds 28 may be desired in that the ice packs will still assume a generally flat configuration, as particularly illustrated in FIG. 2. This provides a convenient configuration for packaging, shipping, and storing the ice packs.

It should be appreciated by those skilled in the art that various modifications and variations can be made in the present invention without departing from the scope and spirit of the invention. For example, various structural configurations may be utilized in the side panels besides the folds illustrated in the figures to provide a greater effective cross-sectional area for the opening. It is intended that the present invention include such modifications and variations as come within the scope of the appended claims and their equivalents.

What is claimed is:

1. An ice pack, comprising:

an elongated bag member defined by opposite side panels having sealed edges and a sealed first end, said bag member configured for receiving and holding ice therein;

an opening defined in a second end of said bag member for introducing ice into said bag member, said opening defined upon pulling said side panels apart at said second end; and wherein a portion of at least one of said side panels generally adjacent said second end is expandable without generally increasing the distance between said sealed edges at said second end so as to provide a greater effective cross-sectional area for said opening to aid in filling said bag member.

2. An ice pack, comprising:

an elongated bag member defined by opposite side panels having sealed edges and a sealed first end, said bag member configured for receiving and holding ice therein;

an opening defined in a second end of said bag member for introducing ice into said bag member, said opening defined upon pulling said side panels apart at said second end;

wherein a portion of at least one of said side panels generally adjacent said second end is expandable so as to provide a greater effective cross-sectional area for said opening to aid in filling said bag member; and wherein said portion comprises a longitudinally extending expandable structure defined in said side panel such that said side panel expands along said expandable structure.

3. The ice pack as in claim 2, wherein said longitudinally extending expandable structure comprises a longitudinally extending gathering of material of said side panel.

4. The ice pack as in claim 3, wherein said gathering comprises at least one longitudinally extending fold line.

5. The ice pack as in claim 4, wherein said fold line comprises multiple folds of said material.

6. The ice pack as in claim 2, wherein said longitudinally extending expandable structure has an effective length less than a full longitudinal length of said side panel.

7. The ice pack as in claim 6, wherein said longitudinally extending expandable structure comprises a longitudinally extending gathering of material of said side panel, said gathering extending generally along the full longitudinal length of said side panel but sealed generally from said first end to a position spaced from said opening.

8. The ice pack as in claim 7, wherein said gathering comprises at least one longitudinally extending fold line.

9. The ice pack as in claim 1, wherein each of said side panels comprises said expandable portion.

10. The ice pack as in claim 2, wherein each of said side panels comprises said longitudinally extending expandable structure.

11. The ice pack as in claim 1, further comprising a closure member configured for sealing said second end.

12. The ice pack as in claim 1, further comprising at least one tie member extending longitudinally from each of said first and second ends.

13. The ice pack as in claim 12, wherein a pair of said tie members extend longitudinally from each of said first and second ends.

14. An ice pack, comprising:

an elongated bag member defined by opposite side panels having sealed edges and a sealed first end, said bag member configured for receiving and holding ice therein;

an opening defined in a second end of said bag member for introducing ice into said bag member, said opening defined upon pulling said side panels apart at said second end; and a longitudinally extending fold line defined in at least one of said side panels and extending from said second end towards said first end, said fold line providing an increased effective cross-sectional area for said opening upon pulling said side panels apart.

15. The ice pack as in claim 14, wherein said fold line has an effective length which is less than the longitudinal distance between said first and second ends.

16. The ice pack as in claim 15, wherein said fold line extends from said first end to said second end and is sealed along a portion thereof from said first end towards said second end such that an unsealed portion thereof extending from said second end towards said first end defines said effective length.

17. The ice pack as in claim 14, wherein each of said side panels includes said longitudinally extending fold line.

18. The ice pack as in claim 14, further comprising tie members extending longitudinally from each of said first and second ends.

* * * * *